United States Patent
Ma et al.

(10) Patent No.: US 10,064,593 B2
(45) Date of Patent: Sep. 4, 2018

(54) IMAGE RECONSTRUCTION FOR A VOLUME BASED ON PROJECTION DATA SETS

(71) Applicant: Siemens Medical Solutions USA, Inc., Malvern, PA (US)

(72) Inventors: Jun Ma, Palatine, IL (US); Alexander Hans Vija, Evanston, IL (US); Amos Yahil, Stony Brook, NY (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 15/317,064

(22) PCT Filed: Jun. 12, 2015

(86) PCT No.: PCT/IB2015/054451
§ 371 (c)(1),
(2) Date: Dec. 7, 2016

(87) PCT Pub. No.: WO2015/189811
PCT Pub. Date: Dec. 17, 2015

(65) Prior Publication Data
US 2017/0105695 A1    Apr. 20, 2017

Related U.S. Application Data

(60) Provisional application No. 62/011,787, filed on Jun. 13, 2014.

(51) Int. Cl.
*G06K 9/00* (2006.01)
*A61B 6/00* (2006.01)
(Continued)

(52) U.S. Cl.
CPC ............ *A61B 6/5205* (2013.01); *A61B 6/032* (2013.01); *A61B 6/0407* (2013.01);
(Continued)

(58) Field of Classification Search
CPC ..... A61B 6/032; A61B 6/0407; A61B 6/4266; A61B 6/5205; G06T 11/006;
(Continued)

(56) References Cited

U.S. PATENT DOCUMENTS

| 5,636,334 A * | 6/1997 | Hidaka | G06T 15/00 |
| | | | 345/419 |
| 7,737,406 B2 * | 6/2010 | Vija | G01T 1/1611 |
| | | | 250/363.04 |

(Continued)

FOREIGN PATENT DOCUMENTS

| HU | 226835 | 12/2009 |
| HU | P0900597 | 1/2011 |

OTHER PUBLICATIONS

Ross et al., "A method of overlap correction for fully 3D OSEM reconstruction of PET data", published in 2004, 2004 IEEE, pp. 3497-3500.*

(Continued)

*Primary Examiner* — Mekonen Bekele

(57) ABSTRACT

Multiple sets of projection data are provided for respective ones of a first set of volumes. An initial image is generated for a second volume larger than each volume in the first set of volumes. Based on at least the initial image and the sets of projection data, an image of the second volume is reconstructed using multiple iterations of a single iterative reconstruction process.

18 Claims, 9 Drawing Sheets

(51) Int. Cl.
    G06T 11/00    (2006.01)
    G06T 7/00     (2017.01)
    G06T 7/70     (2017.01)
    A61B 6/03     (2006.01)
    A61B 6/04     (2006.01)

(52) U.S. Cl.
    CPC .......... A61B 6/4266 (2013.01); G06T 7/0012 (2013.01); G06T 7/70 (2017.01); G06T 11/008 (2013.01); *G06T 2207/10072* (2013.01); *G06T 2207/30004* (2013.01)

(58) Field of Classification Search
    CPC ....... G06T 11/008; G06T 7/0012; G06T 7/70; G06T 2207/10072; G06T 2207/30004; G06T 2211/424; G06T 2211/432
    See application file for complete search history.

(56) References Cited

U.S. PATENT DOCUMENTS

| | | | |
|---|---|---|---|
| 9,655,563 B2* | 5/2017 | Liu | A61B 5/7267 |
| 2007/0183642 A1* | 8/2007 | Ye | G06T 11/006 |
| | | | 382/131 |
| 2008/0095414 A1* | 4/2008 | Desh | G06T 11/006 |
| | | | 382/128 |
| 2008/0219534 A1* | 9/2008 | Faul | A61B 6/032 |
| | | | 382/131 |
| 2010/0032575 A1* | 2/2010 | Iagaru | A61B 6/032 |
| | | | 250/362 |
| 2012/0155736 A1* | 6/2012 | Faul | A61B 6/032 |
| | | | 382/131 |
| 2014/0276032 A1* | 9/2014 | Majewski | A61B 6/0407 |
| | | | 600/431 |
| 2015/0087957 A1* | 3/2015 | Liu | G06T 7/42 |
| | | | 600/408 |
| 2016/0371862 A1* | 12/2016 | Silver | G06T 11/008 |
| 2017/0098316 A1* | 4/2017 | Ma | G06T 11/006 |

OTHER PUBLICATIONS

Search Report for Corresponding Hungarian Patent Application No. P1700010, dated Mar. 22, 2017.
Ross, S., et al. "A method of overlap correction for fully 3D OSEM reconstruction of PET data", 2004 IEEE Nuclear Science Symposium Conference Record Oct. 16-22, 2004 Rome, Italy, IEEE, Piscataway, NJ, USA, vol. 6, Oct. 16, 2004, pp. 3497-3500.
International PCT Search Report and Written Opinion dated Oct. 13, 2015 (9 pages).

* cited by examiner

IMAGE RECONSTRUCTION FOR A VOLUME BASED ON PROJECTION DATA SETS

CROSS-REFERENCE TO RELATED APPLICATION

This application claims priority under 35 U.S.C. § 119(e) from U.S. Provisional Application Ser. No. 62/011,787 filed Jun. 13, 2014, the entirety of which is hereby incorporated by reference herein.

FIELD

Aspects of the present disclosure relate in general to image reconstruction for a volume based on projection data, and more particularly to image reconstruction that results in images having improved quality and quantitative accuracy, among other advantages over traditional imaging approaches.

BACKGROUND

Imaging of objects is useful in a variety of contexts. In the medical context, imaging of patients plays an important role in numerous scenarios. Medical imaging of metabolic and biochemical activity within a patient is known as functional imaging. Functional imaging techniques include, for example, nuclear imaging such as Positron Emission Tomography (PET), Single Photon Computed Tomography (SPECT), functional magnetic resonance imaging (fMRI), and functional computed tomography (fCT). An overview of SPECT, PET systems, their combination with computer tomography (CT) systems as well as iterative image reconstruction for emission tomography is given in chapter 7, chapter 11, and chapter 21 of M. Wernick and J. Aarsvold, "Emission tomography: the fundamentals of PET and SPECT," Elsevier Academic Press, 2004, the contents of which are herein incorporated by reference.

As just one example of medical imaging, SPECT imaging, is performed by using a gamma camera to acquire multiple projections in one space (e.g., 2D space) and then using a computer to perform tomographic image reconstruction to generate an image in a higher-dimensional (e.g., 3D or 4D) space. For example, a gamma photon-emitting radioisotope may be introduced into a patient's body, and any of various techniques can be used to bind the radioisotope to a location of interest in the body. The patient lies on a bed that is positioned at a given bed position. One or more gamma cameras are attached to the gantry, and the gantry rotates and/or shifts, causing the gamma camera(s) to rotate and/or shift relative to the patient. Detectors of the gamma camera(s) acquire projection data at each orientation by detecting gamma photons emitted by the radioisotope, resulting in a projection data set for this bed position.

In this manner, a portion of the body (e.g., heart) of the patient can be imaged to yield a 3D or 4D (e.g., three spatial dimensions plus time dimension) image that can be displayed in various ways, e.g., by showing various projections as requested by an operator. If imaging is then desired for another portion of the body (e.g., abdomen), it may be necessary to move the bed supporting the patient to a new bed position, so that the other portion of the body is now capable of being imaged. Multi-bed imaging has been used for this purpose. Traditionally, for multi-bed imaging, projection data are acquired for patient lying on a bed situated at a first bed position, and tomographic reconstruction is performed using that projection data to generate a first image. Then, the bed is moved to a second bed position. For convenience, this may be referred to as a second bed, although it is understood that the same bed has simply been moved to a new position. The first and second bed positions may also be referred to as first and second imaging positions because projection data used for imaging are acquired at those positions.

New projection data are acquired for the second bed (i.e., at the second imaging position), and reconstruction is performed using the new projection data to generate a second image. The axial edge typically has an inconsistency as the collimator with its 3D point response function (axial and transaxial) can receive counts from outside the field of view (FOV). This inconsistency is reflected in the image as artifacts. One technique for mitigating such artifacts is to simply restrict the useful axial FOV, or to employ techniques that only minimize the axial edge artifacts. When creating a volume out of multiple bed positions, such as the first and second bed positions described above, the image volumes are overlapped. The overlap function can either be a sharp cutoff or some interpolation.

One drawback of traditional multi-bed imaging is that combining two 3D images as described above often results in inconsistencies, both visually and quantitatively, at the interface of the regions of the patient's body corresponding to respective beds.

SUMMARY

In some embodiments of the present disclosure, a method for image generation includes providing multiple sets of projection data for respective ones of a first set of volumes. An initial image is generated for a second volume larger than each volume in the first set of volumes. Based on at least the initial image and the sets of projection data, an image of the second volume is reconstructed using multiple iterations of a single iterative reconstruction process.

In some embodiments, an imaging system includes a plurality of detectors connected to a gantry, a bed capable of supporting a patient, a machine-readable storage medium, and a processor connected to and in communication with said detectors. The machine-readable storage medium is encoded with a computer program code such that, when the computer program code is executed by the processor, the processor performs operations comprising: at each of a plurality of bed positions, acquiring a set of projection data for a portion of the body of the patient lying on the bed, wherein the sets of projection data are acquired using the plurality of detectors; generating an initial image for a volume including at least the portions of the body corresponding to the sets of projection data; and based on at least the initial image and the sets of projection data, reconstructing an image of the volume using multiple iterations of a single iterative reconstruction process.

In some embodiments, a machine-readable storage medium tangibly embodies a program of instructions executable by a processor to cause the processor to perform various operations. The instructions are executable by the processor to cause the processor to provide a plurality of sets of projection data for respective ones of a first set of volumes; generate an initial image for a second volume larger than each volume in the first set of volumes; and based on at least the initial image and the sets of projection data, reconstruct an image of the second volume using multiple iterations of a single iterative reconstruction process.

BRIEF DESCRIPTION OF THE DRAWINGS

The following will be apparent from elements of the figures, which are provided for illustrative purposes and are not necessarily to scale.

DETAILED DESCRIPTION

This description of the exemplary embodiments is intended to be read in connection with the accompanying drawings, which are to be considered part of the entire written description.

Figure 1:
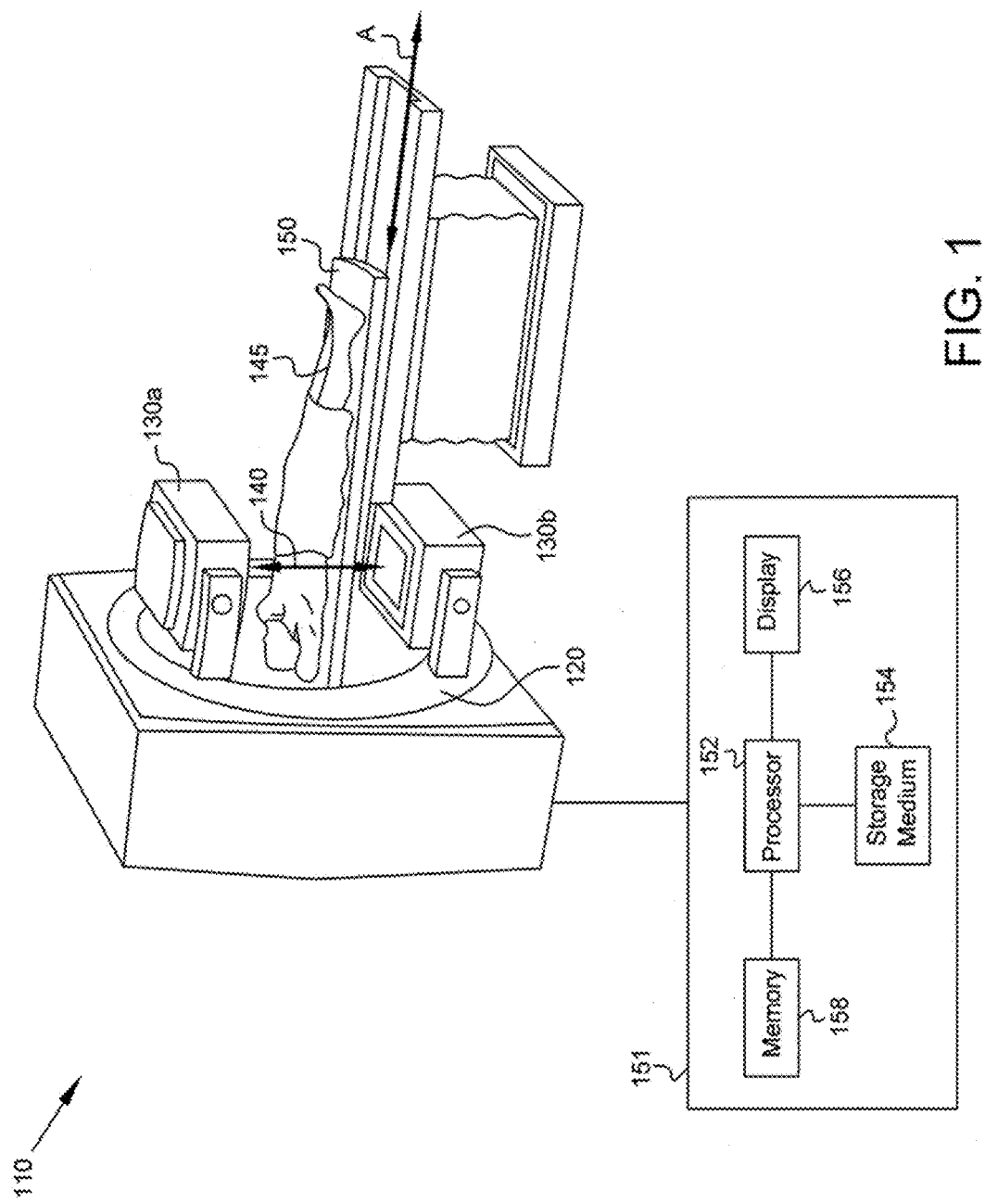
FIG. 1 is a diagram of a SPECT scanner system in accordance with some embodiments of the present disclosure.

FIG. 1 is a diagram of an imaging system 110 in accordance with some embodiments of the present disclosure. Imaging system 110 may be a SPECT scanner system, for example. For ease of explanation, a SPECT scanner system is discussed herein, although in some embodiments an imaging system that does not rely on nuclear medical imaging or on a patient lying on a bed may be used. SPECT scanner system 110 includes a gantry 120 to which one or more gamma cameras are attached. Two gamma cameras 130a, 130b (collectively, gamma cameras 130) are shown in FIG. 1, although other numbers of gamma cameras may be used. Detectors in the gamma cameras detect gamma photons 140 emitted by a radioisotope within the body of a patient 145 lying on a bed 150. A computer 151 may control the operation of the gamma cameras. Bed 150 is slidable along an axis of motion A. At a given bed position, a portion of the body of patient 145 is between gamma cameras 130 and is thus capable of being imaged. The respective bed positions may be referred to as imaging positions.

Gamma cameras 130 rotate around the patient's body. In some embodiments, such rotation is a 3D rotation that may include shifts. Projection data are acquired at defined points during the rotation and are stored in a memory 158 of computer 151. Computer 151 may also include a processor 152, a non-transitory computer readable storage medium 154, and a display 156. Processor 152 executes instructions (described further below) stored on storage medium 154 and manipulates data stored at memory 158, to reconstruct a 3D image from the acquired projection data. The reconstructed 3D image may be displayed on a display 156.

In contrast to the traditional approach of reconstructing an image volume corresponding to each bed separately and then joining the separate volumes post-reconstruction, in various embodiments of the present disclosure a single image volume is reconstructed in a single image reconstruction process using the projection data sets acquired from multiple beds, enabling the reconstruction to optimally create the image volume given the multiple bed data. Because in some embodiments the projection operation is fully in 3D, the reconstruction process can optimize 3D rotations/shifts for each bed, so as to result in one consistent image volume given the data from multiple beds. Image quality and quantitative accuracy are improved relative to the traditional approach of joining separate volumes post-reconstruction. Additionally, FOV is maximized, in comparison to the traditional approach which limits the axial FOV to minimize edge artifacts.

Figure 2:
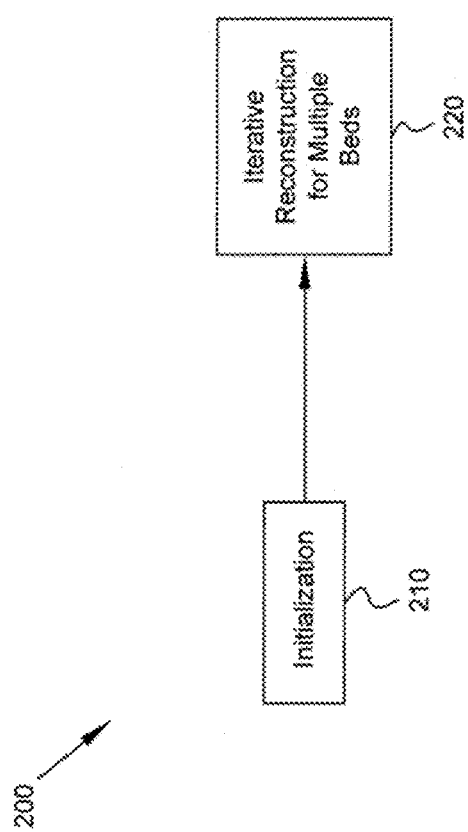
FIG. 2 is a flow diagram of a process in accordance with some embodiments.
Figure 3:
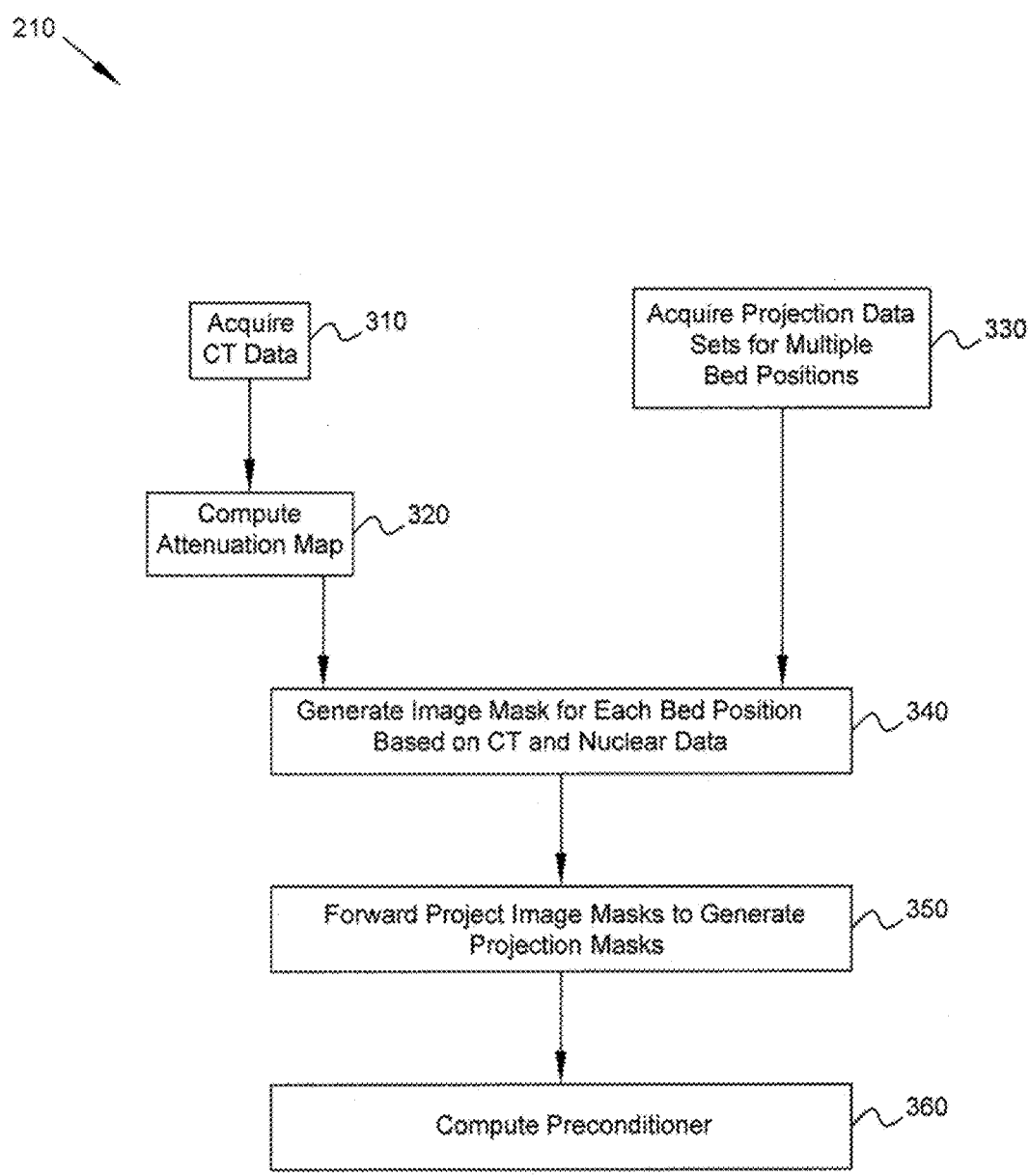
FIG. 3 illustrates processing during initialization in accordance with some embodiments.
Figure 6A:
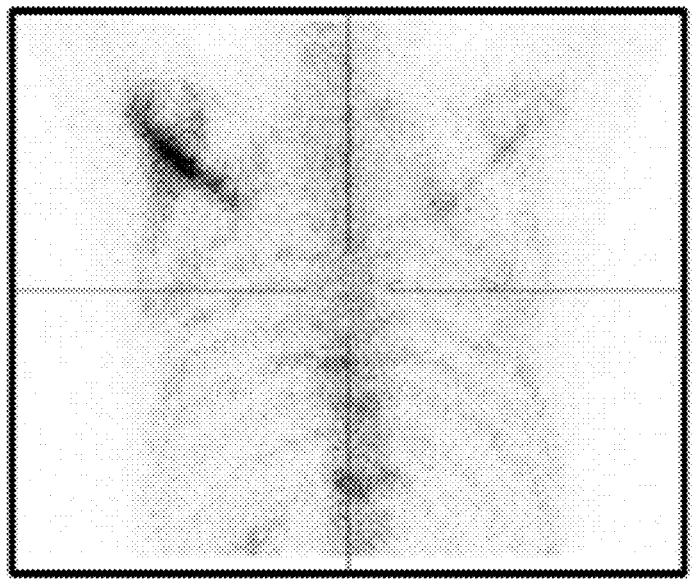
FIGS. 6A-6B show acquired nuclear data for a pair of beds in accordance with some embodiments.
Figure 6B:
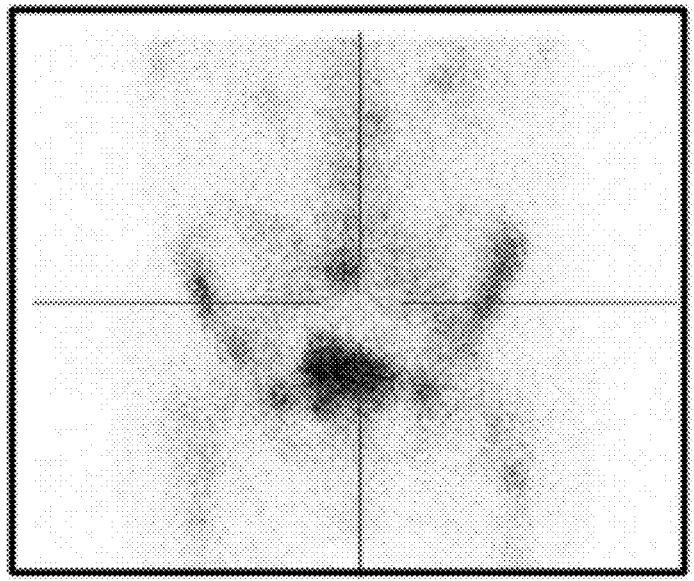

FIG. 2 is a flow diagram of a process 200 in accordance with some embodiments. Computations in blocks 210 and 220 may be performed by processor 152. Initialization process 210 includes initializing an image (e.g., 3D or 4D image) and other parameters that will be used during iterative reconstruction. FIG. 3 includes details regarding initialization 210 in some embodiments. Processing during initialization does not have to occur in the order depicted in FIG. 3. As part of the initialization 210, a portion of the patient's body is imaged, e.g., using computed tomography (CT) (block 310), and an attenuation map is computed (320). At block 330, projection data sets are acquired for multiple (N>1) imaging positions, e.g., bed positions (block 310). For example, bed 150 may be positioned at a first bed position $p_1$, and a set of projection data $D_1$ are acquired by gamma cameras 130 as described above. The bed is sequentially translated to various bed positions, with a set of projection data $D_k$ acquired at each bed position $p_k$. Thus, projection data sets $D_1, \ldots, D_N$ are acquired as the bed position is iterated. Projection data sets $D_1, \ldots, D_N$ correspond to projections of respective volumes in a first set of volumes. Without loss of generality, suppose N=2 for ease of explanation, in which case the projection data sets are $D_1$ and $D_2$. An example projection from projection data set $D_1$ is shown in FIG. 6A, and an example projection from projection data set $D_2$ is shown in FIG. 6B.

System matrices $H_k$ for each bed position $p_k$ (more generally, for each imaging position) are determined using standard techniques. In general, for image reconstruction, object space and data space are related to each other through a system matrix. One of ordinary skill in the art recognizes that the system matrix takes into account various factors such as PRF (which is the same for each bed position, and which can be measured at part of an initial calibration process), attenuation map, and scatter estimates. For any projection operation, one can use the appropriate system matrix and its transpose to transform objects between object space and data space. In general, a forward projection is an application of the appropriate system matrix to an object in object space. The result of a forward projection is a "projected object" in data space. As an example in nuclear imaging, a forward projection is the linear operation that transforms the functional activity density into the total data model of predicted detection events. Corresponding to the forward projection, the backward projection from the data space into object space can be described as an application of the transpose of the appropriate system matrix.

In some embodiments, bed deflection is modeled based on a series of measurements as functions of patient weight and bed position. Deflection measurements can be incorporated into system matrices $H_k$ corresponding to respective bed positions $p_k$.

As discussed in greater detail below, an initial image is generated for a second volume larger than each volume in the first set of volumes. Then, based on at least the initial image and the sets of projection data, an image of the second volume is reconstructed using multiple iterations of a single iterative reconstruction process. In this way, a larger volume (here, the second volume) can be reconstructed using projection data sets corresponding to smaller volumes in an efficient, accurate, high-quality manner. Unlike traditional approaches, reduction in size of a to-be-imaged volume is not needed. Instead, separately acquired projection data sets which correspond to respective volumes can be used in a single reconstruction process to generate the larger second volume.

Figure 4:
FIG. 4 is an example CT image that may be used for initialization in accordance with some embodiments.
Figure 5A:
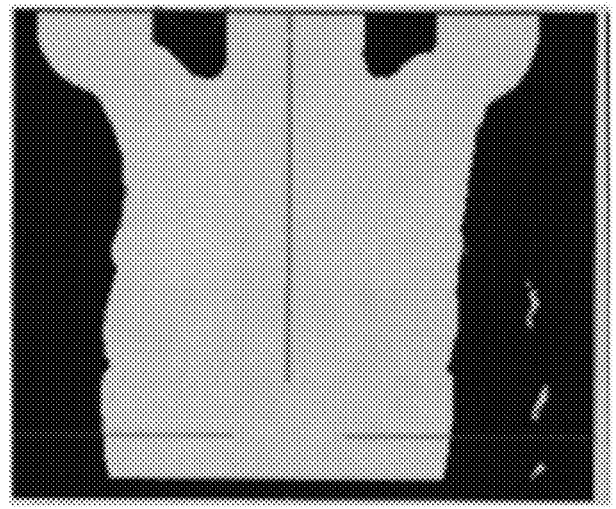
FIGS. 5A-5B show image masks for a pair of bed positions in accordance with some embodiments.
Figure 5B:
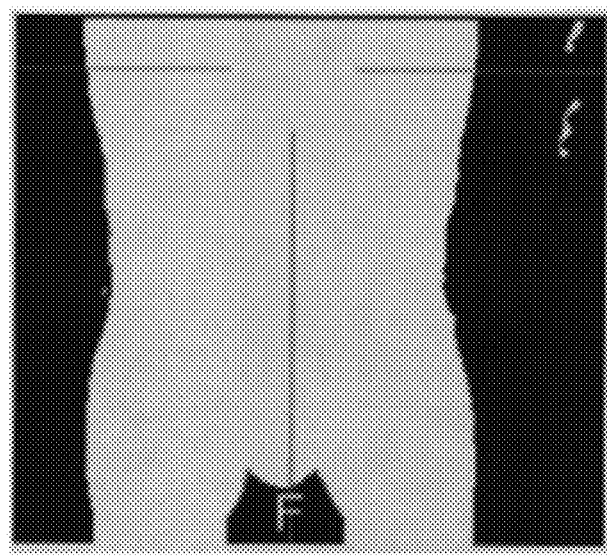

Details of one possible implementation are provided herein by way of example but are not limiting. In one example implementation, an image mask $M_k$ is generated for each bed position $p_k$ (more generally, for each imaging position) in some embodiments (block 340). The image masks may be generated based on a previously computed 3D image such as a CT image shown in FIG. 4. FIGS. 5A and 5B show image masks for respective beds (i.e., a bed positioned at respective bed positions). The image masks in FIGS. 5A-5B may be generated by selecting a subset of the CT image with the range (vertical dimension in FIGS. 5A-5B) determined by nuclear data, i.e., range corresponding to the respective bed for which nuclear data is depicted in FIG. 6A or 6B. The CT image data used for the image masks may be processed to generate, e.g., one value for voxels within the body and another value for voxels outside the body, as shown in FIG. 5A-5B. Thus, the voxel values in the image masks may differentiate between voxels within the body of the patient and voxels outside the body of the patient.

In some embodiments, each image mask $M_k$ is forward projected with the corresponding system matrix $H_i$ to generate a projection mask $P_k$ for bed position $p_k$, i.e., for the $k^{th}$ bed (block 350) (more generally, for the $k^{th}$ imaging position), e.g., according to the following expression:

$$P_k = H_k M_k \quad (1)$$

The image masks $M_k$ may also be forward projected and back projected to generate a preconditioner, e.g., according to the following expression:

$$\eta = 1/(\Sigma_k H_k^T W_k H_k M_k) \quad (2)$$

In equation (2), $W_k$ is a weighting function for the $k^{th}$ bed (more generally, for the $k^{th}$ imaging position). Any of various known weighting functions may be used, and the weighting function is part of the merit function used for optimization, so various merit functions may be used. For example, some embodiments use a modified chi-square-gamma statistic as described in K. J. Mighell, "Parameter estimation in astronomy with Poisson-distributed data. I. The $\chi_\gamma^2$ statistic," Astrophys. J., 1999, 518: 380-393 and K. J. Mighell, "Parameter estimation in astronomy with Poisson-distributed data. II. The modified chi-square gamma statistic", 2000, arXiv:astro-ph/0007328, the contents of which are herein incorporated by reference.

In some embodiments, the preconditioner $\eta$ has the same dimensions as the final image outputted by the reconstruction process.

The projection masks $P_k$ and preconditioner $\eta$ may be used during iterative reconstruction as discussed further below.

Figure 7:
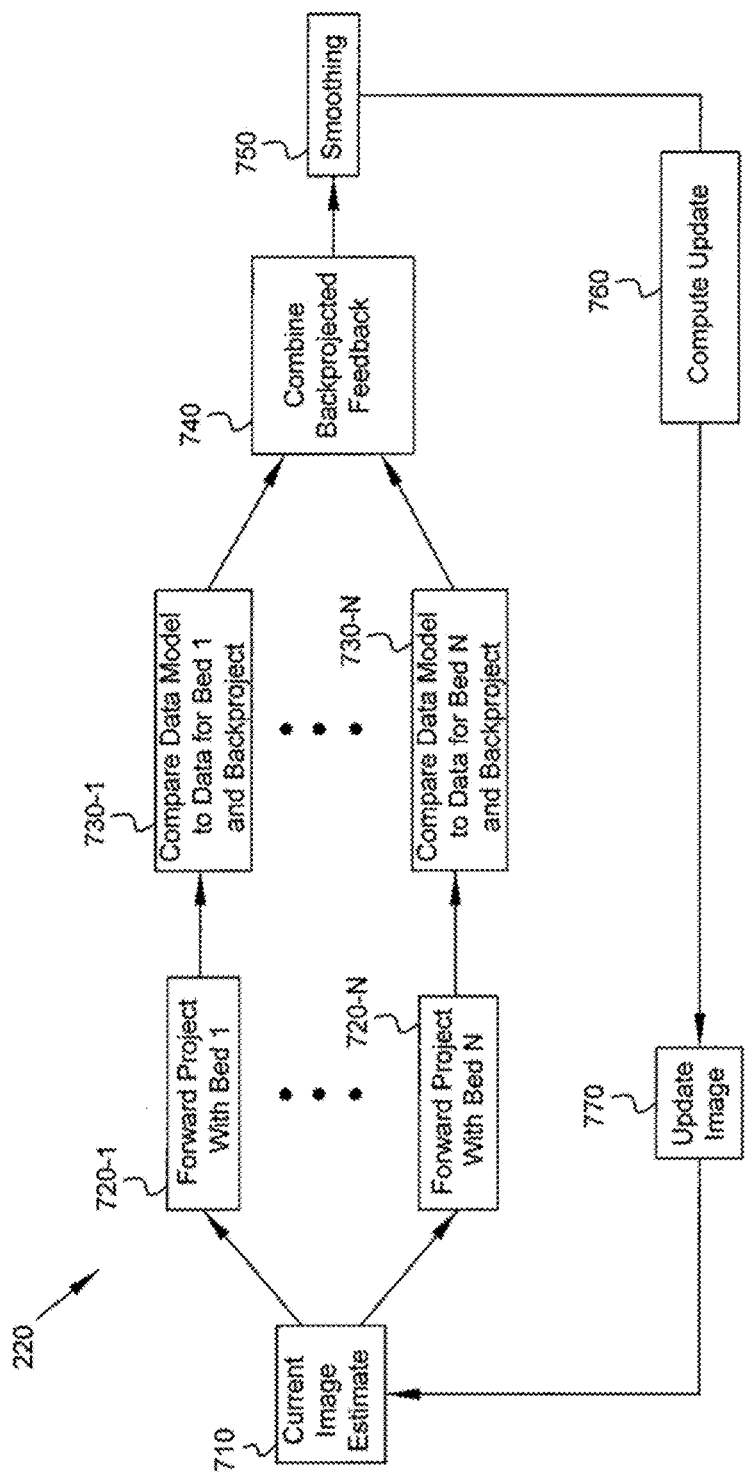
FIG. 7 is a flow diagram of iterative image reconstruction in accordance with some embodiments.

Referring back to FIG. 2, after initialization 210, a single iterative reconstruction process 220 is performed for multiple beds. Beginning with a current image estimate I (block 710), various processing is performed in a feedback loop as shown in FIG. 7 for multiple iterations. The image estimate I may be initialized based on image masks derived from 3D CT image data as in FIGS. 5A-5B One iteration of the iterative reconstruction loop is now described. The current image estimate I is forward projected with the system matrix $H_k$ corresponding to the $k^{th}$ bed (i.e., to each bed position), to generate a set of data models $D'_k$, at blocks 720-1, ..., 720-N. These forward projections may be expressed as:

$$D'_k = H_k I \quad (3)$$

The forward projections are thus transformations using the bed-dependent system matrices (more generally, imaging position-dependent system matrices), which in turn take into account factors such as the attenuation map and scatter estimates.

At blocks 730-1, ..., 730-N, a data model is compared to projection data for respective beds (more generally, for respective imaging positions), and the result of the comparison is backprojected into object space. For example, this comparison may be implemented as a gradient computation such as:

$$G_k = H_k^T W_k (D_k - D'_k) \quad (4)$$

Thus, forward projections and gradient computations for each bed are performed within the context of a single iterative reconstruction process (i.e., to refine a single 3D image estimate I), unlike traditional approaches that generate separate reconstructed images for each bed position and then attempt to combine the individual reconstructed images.

In some embodiments, between blocks 720-$i$ and 730-$i$ (for each $i$), the projection masks $P_k$ are applied to the respective data models $D'_k$. In other words, the projection masks $P_k$ are multiplied by the corresponding data models in projection space after forward projection of the current image estimate with the corresponding system matrix and before the gradient computation.

In some embodiments, at block 740, backprojected feedback resulting from each of blocks 730-1, ..., 730-N are combined. For example, gradient data corresponding to various beds may be combined, and the preconditioner $\eta$ computed during initialization 210 may be applied, to generate combined data G. In one example implementation, computation at block 740 may be expressed as:

$$G = \eta \Sigma_k G_k \quad (5)$$

Thus, backprojected feedback associated with respective beds (more generally, respective imaging positions) are combined using the preconditioner $\eta$. One of ordinary skill in the art recognizes that the arithmetic operations in various mathematical expressions disclosed herein may be implemented in various ways. For example, multiplication by preconditioner $\eta$ to yield combined data G may occur within block 740 as part of computation (5) or may be performed separately.

Smoothing may be applied at block 750, e.g., pixon or Gaussian smoothing. At block 760, an update is computed, e.g., according to the following expression, with "old" and "new" in the superscripts for variables referring to previous and present iterations of the reconstruction loop:

$$K^{new} = \gamma K^{old} + G \quad (6)$$

One of ordinary skill recognizes that other implementations for the update may be used as well. $K^{new}$ and $K^{old}$ are each matrices with the same dimensions as image I. K may be initialized with combined data G. In equation (6), γ may be computed as follows:

$$\gamma = (G^{new} - G^{old})^T G^{new} / \|G^{old}\|^2 \quad (7)$$

A step size may be computed according to the following expression:

$$\delta = [\Sigma_k (H_k K^{new})^T W_k (D_k - D'_k)] \Sigma_k \|H_k K^{new}\|^2 \quad (8)$$

At block 770, the image estimate is updated, e.g., as follows:

$$I^{new} = I^{old} + \delta K^{new} \quad (9)$$

Figure 8:
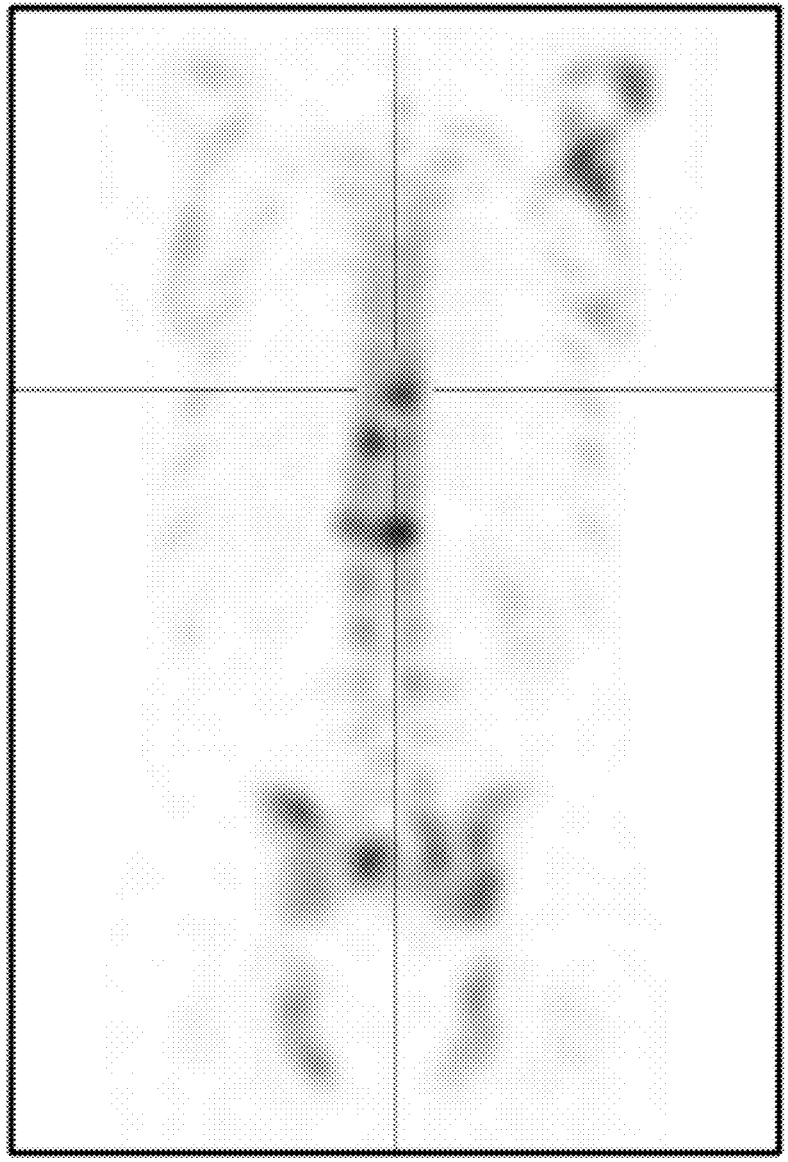
FIG. 8 is an example reconstructed 3D image in accordance with some embodiments.

Multiple iterations of the iterative reconstruction loop are performed. In some embodiments, a fixed number of iterations such as N=24 or 48 iterations are performed. In other embodiments, the number of iterations may be based on a convergence criterion. After the iterative reconstruction process 220 is concluded, post-processing of the final image estimate I may be performed. For example, isotropic resampling and post smoothing may be performed. A 2D projection of an example resulting output 3D image is shown in FIG. 8. This 3D image may be displayed in various ways on display 156. Alternatively, the result of the reconstruction may be a 4D image, which may be displayed on display 156, e.g., as a sequence of frames.

Thus, iterative image reconstruction of a single image corresponding to multiple beds is performed in some embodiments. Reconstruction in accordance with various embodiments is more efficient and yields better quality images, with fewer visual and quantitative inconsistencies, than prior approaches. Although a particular implementation is detailed above regarding initialization and iterative image reconstruction, other implementations can be used as well. For example, although projection data are described in examples herein as corresponding to respective bed positions of a bed, more generally the projection data may be obtained at respective imaging positions using any suitable projection technique and any suitable projection apparatus. For example, in some embodiments a projection technique that does not use nuclear imaging principles may be used. In some embodiments, a bed does not need to translate along an axis, or there may not be a bed at all.

Figure 9:
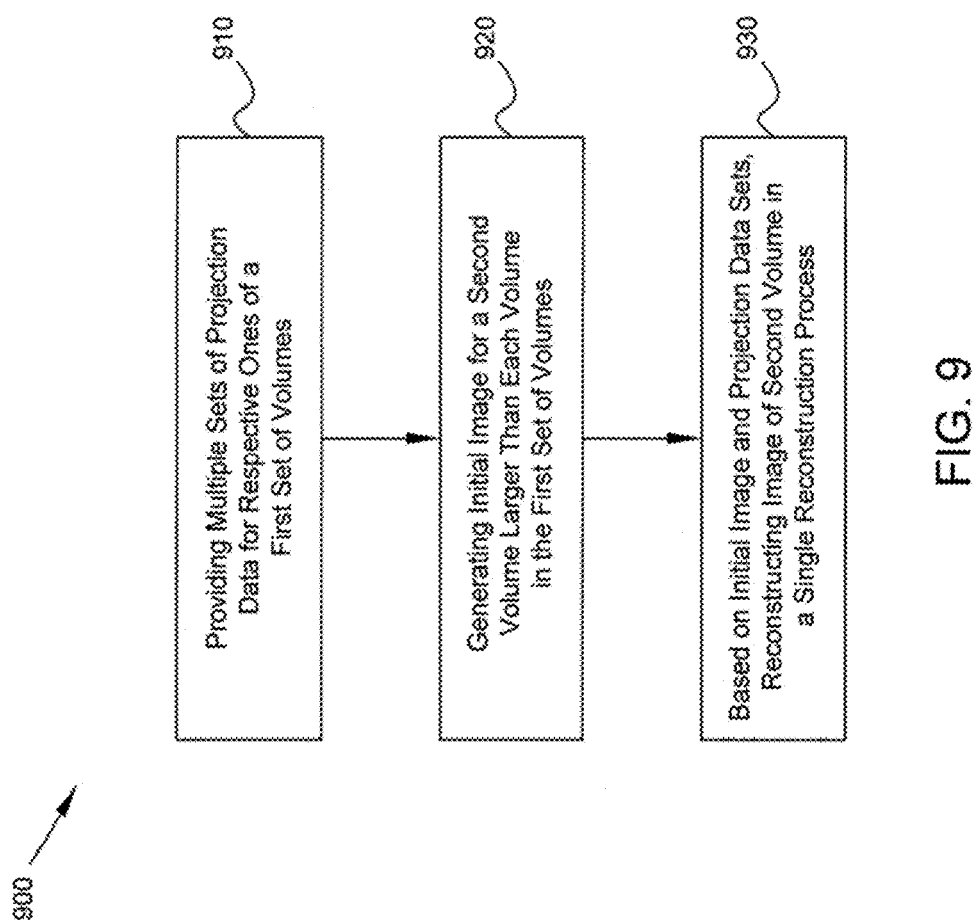
FIG. 9 is a flow diagram of a process in accordance with some embodiments.

FIG. 9 is a flow diagram of a process in accordance with some embodiments. Process 900 includes. providing multiple sets of projection data for respective ones of a first set of volumes (block 910). The projection data sets may be acquired at respective imaging positions, e.g., bed positions of a bed supporting a patient. An initial image is generated (block 920) for a second volume larger than each volume in the first set of volumes. Based on at least the initial image and the sets of projection data, an image of the second volume is reconstructed (block 930) using multiple iterations of a single iterative reconstruction process. The reconstructed image of the second volume may be a 3D or 4D image (e.g., a 3D or 4D SPECT image) and may be displayed on display 156.

In some embodiments, storage medium 154 tangibly embodies a program of instructions executable by processor 152 to cause processor 152 to perform operations in process 900 as well as various other processing described herein.

It is understood by those familiar with the art that techniques described herein may be implemented in hardware, firmware, or software encoded (e.g., as instructions executable by a processor) on a non-transitory computer-readable storage medium.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method for image generation, the method comprising:
   providing a plurality of sets of projection data for respective ones of a first set of volumes;
   acquiring the sets of projection data at respective ones of N imaging positions by generating an image mask for each of a plurality of imaging positions, N being an integer;
   generating an initial image for a second volume larger than each volume in the first set of volumes;
   based on at least the initial image and the sets of projection data, reconstructing an image of the second volume using multiple iterations of a single iterative reconstruction process;
   computing a preconditioner η according to: $\eta = 1/(\Sigma_{k,l} H_k^T W_k H_k M_k)$,
   where k ranges from 1 to N, $H_k$ denotes a system matrix associated with the $k^{th}$ imaging position, W denotes a weighting function, and $M_k$ denotes the $k^{th}$ image mask; and
   during the iterative reconstruction process, combining backprojected feedback associated with respective imaging positions using the preconditioner.

2. The method of claim 1, the reconstruction process including:
   for each imaging position among the N imaging positions, forward projecting an image estimate with a system matrix associated with said imaging position, to generate a plurality of N data models.

3. The method of claim 2, wherein the reconstruction process further includes:
   based on at least the data models, the sets of projection data, and system matrices associated with respective imaging positions, computing backprojected feedback associated with respective imaging positions.

4. The method of claim 3, wherein the reconstruction process further includes combining the backprojected feedback associated with respective imaging positions.

5. The method of claim 1, wherein the image masks are generated based on a computed tomography (CT) image, and each image mask overlaps in range with at least one other image mask.

6. The method of claim 1, wherein each image mask has a first value at each voxel within the second volume and a second value at each voxel outside the second volume.

7. The method of claim 1, the method further comprising:
   for each imaging position among the N imaging positions, forward projecting the corresponding image mask with a system matrix associated with said imaging position, to generate a plurality of N projection masks.

8. The method of claim 7, further comprising:
for each imaging position among the N imaging positions, forward projecting an image estimate with the system matrix associated with said imaging position, to generate a plurality of N data models; and
for each imaging position among the N imaging positions, multiplying the corresponding data model by the corresponding projection mask.

9. The method of claim 1, further comprising:
for each imaging position among the N imaging positions, forward projecting an image estimate with the system matrix corresponding to said imaging position, to generate a plurality of N data models;
based on at least the data models, the sets of projection data, and the system matrices, computing the backprojected feedback associated with respective imaging positions; and
combining the backprojected feedback associated with respective imaging positions, to generate combined data, according to: $G=\eta\Sigma_k G_k$,
wherein G represents the combined data, k ranges from 1 to N, and $G_k$ represents the backprojected feedback associated with the $k^{th}$ imaging position.

10. An imaging system comprising:
a plurality of detectors connected to a gantry;
a bed capable of supporting a patient;
a non-transitory computer-readable storage medium; and
a processor connected to and in communication with said detectors, wherein the non-transitory computer-readable storage medium is encoded with computer executable instructions such that, when the computer executable instructions are executed by the processor, the processor performs operations comprising:
at each of a plurality of bed positions, acquiring a set of projection data for a portion of the body of the patient lying on the bed, wherein the sets of projection data are acquired using the plurality of detectors;
the set of projection data is acquired at respective ones of N imaging positions by generating an image mask for each of a plurality of imaging positions, N being an integer;
generating an initial image for a volume including at least the portions of the body corresponding to the sets of projection data;
based on at least the initial image and the sets of projection data, reconstructing an image of the volume using multiple iterations of a single iterative reconstruction process;
computing a preconditioner $\eta$ according to: $\eta=1/(\Sigma_{k} H_k^T W_k H_k M_k)$,
where k ranges from 1 to N, $H_k$ denotes a system matrix associated with the $k^{th}$ imaging position, W denotes a weighting function, and $M_k$ denotes the $k^{th}$ image mask; and
during the iterative reconstruction process, combining backprojected feedback associated with respective imaging positions using the preconditioner.

11. The imaging system of claim 10, wherein the plurality of bed positions includes N bed positions, and when the computer executable instructions are executed by the processor, the processor further performs operations comprising:
generating an image mask for each of the N bed positions, each image mask comprising a plurality of voxels having values that differentiate between voxels within the body of the patient and voxels outside the body of the patient;
wherein the initial image is generated based on the image masks.

12. The imaging system of claim 10, wherein the plurality of bed positions includes N bed positions, and when the computer executable instructions are executed by the processor, the processor performs operations comprising:
for each bed position among the N bed positions, forward projecting an image estimate with a system matrix associated with said bed position, to generate N data models.

13. The imaging system of claim 12, wherein when the computer executable instructions are executed by the processor, the processor performs operations comprising:
based on at least the data models, the sets of projection data, and system matrices associated with respective bed positions, computing the backprojected feedback associated with respective bed positions.

14. The imaging system of claim 13, wherein when the computer executable instructions are executed by the processor, the processor combines the backprojected feedback associated with respective bed positions.

15. A non-transitory computer-readable storage medium having stored thereon instructions executable by a processor to cause the processor to perform operations comprising:
providing a plurality of sets of projection data for respective ones of a first set of volumes;
acquiring the sets of projection data at respective ones of N imaging positions by generating an image mask for each of a plurality of imaging positions, N being an integer;
generating an initial image for a second volume larger than each volume in the first set of volumes;
based on at least the initial image and the sets of projection data, reconstructing an image of the second volume using multiple iterations of a single iterative reconstruction process;
computing a preconditioner $\eta$ according to: $\eta=1/(\Sigma_{k} H_k^T W_k H_k M_k)$,
where k ranges from 1 to N, $H_k$ denotes a system matrix associated with the $k^{th}$ imaging position, W denotes a weighting function, and $M_k$ denotes the $k^{th}$ image mask; and
during the iterative reconstruction process, combining backprojected feedback associated with respective imaging positions using the preconditioner.

16. The storage medium of claim 15, the instructions further executable to cause the processor to perform operations comprising:
each image mask comprising a plurality of voxels having values that differentiate between voxels within the second volume and voxels outside the second volume;
wherein the initial image is generated based on the image masks.

17. The storage medium of claim 15, the instructions are executable to cause the processor to perform operations comprising:
for each imaging position among the N imaging positions, forward projecting an image estimate with a system matrix associated with said imaging position, to generate N data models.

18. The storage medium of claim 17, wherein the instructions are executable to cause the processor to perform operations comprising:
based on at least the data models, the sets of projection data, and system matrices associated with respective imaging positions, computing backprojected feedback associated with respective imaging positions.

* * * * *